United States Patent [19]

Butler et al.

[11] Patent Number: 5,118,891
[45] Date of Patent: Jun. 2, 1992

[54] SYNGAS CONVERSION CATALYST, PRODUCTION AND USE THEREOF

[75] Inventors: Graham Butler, Godalming; Malcolm P. Heyward, Camberley, both of England

[73] Assignee: The British Petroleum Company p.l.c., London, England

[21] Appl. No.: 739,777

[22] Filed: Jul. 30, 1991

Related U.S. Application Data

[60] Continuation of Ser. No. 647,693, Jan. 28, 1991, abandoned, which is a continuation of Ser. No. 563,825, Aug. 3, 1990, abandoned, which is a continuation of Ser. No. 308,106, Feb. 24, 1989, abandoned, which is a division of Ser. No. 124,843, Aug. 5, 1987, Pat. No. 4,826,803.

[30] Foreign Application Priority Data

Jan. 9, 1986 [GB] United Kingdom ............ 86/004445

[51] Int. Cl.$^5$ .............................................. C07C 1/04
[52] U.S. Cl. ................................. 518/709; 518/715; 518/717
[58] Field of Search ................. 518/709, 715, 717

[56] References Cited

U.S. PATENT DOCUMENTS

| | | |
|---|---|---|
| 2,358,050 | 9/1944 | Boulet . |
| 2,572,633 | 10/1951 | Lanning . |
| 2,620,346 | 12/1952 | Rubin et al. . |
| 4,001,143 | 1/1977 | McCann, III . |
| 4,060,500 | 11/1977 | Clavenna . |
| 4,172,849 | 10/1979 | Drake ........................... 502/304 X |
| 4,755,537 | 7/1988 | Cotton et al. . |

FOREIGN PATENT DOCUMENTS

| | | | |
|---|---|---|---|
| 0169743 | 1/1986 | European Pat. Off. . | |
| 25-18380 | 2/1950 | Japan ................... | 502/304 |
| 56-81392 | 7/1981 | Japan ................... | 502/304 |
| 2119277 | 11/1983 | United Kingdom . | |

Primary Examiner—Howard T. Mars
Attorney, Agent, or Firm—Brooks Haidt Haffner & Delahunty

[57] ABSTRACT

A composition for use after reductive activation as a catalyst in the conversion of synthesis gas to hydrocarbons, the composition having formula: $Ru_zA_bCeO_x$, wherein A is an alkali metal, x is a number such that the valence requirements of the other elements for oxygen is satisfied, a is greater than zero and less than 5% w/w, based on the total weight of the composition, b is in the range from zero to 10% w/w, based on the total weight of the composition, and Ce and O constitute the remainder of the composition, is produced by the steps of: (A) adding a solution or solutions of soluble compounds of the metals ruthenium and cerium, and optionally also an alkali metal compound, to a solution of a precipitant comprising a carbonate and/or a bicarbonate and/or a hydroxide of an alkali metal or ammonium under conditions whereby there is formed a precipitate comprising ruthenium and cerium, and optionally also an alkali metal, in the form of compounds thermally decomposable to the metals and/or their oxides, and (B) recovering the precipitate obtained in step (A).

4 Claims, 2 Drawing Sheets

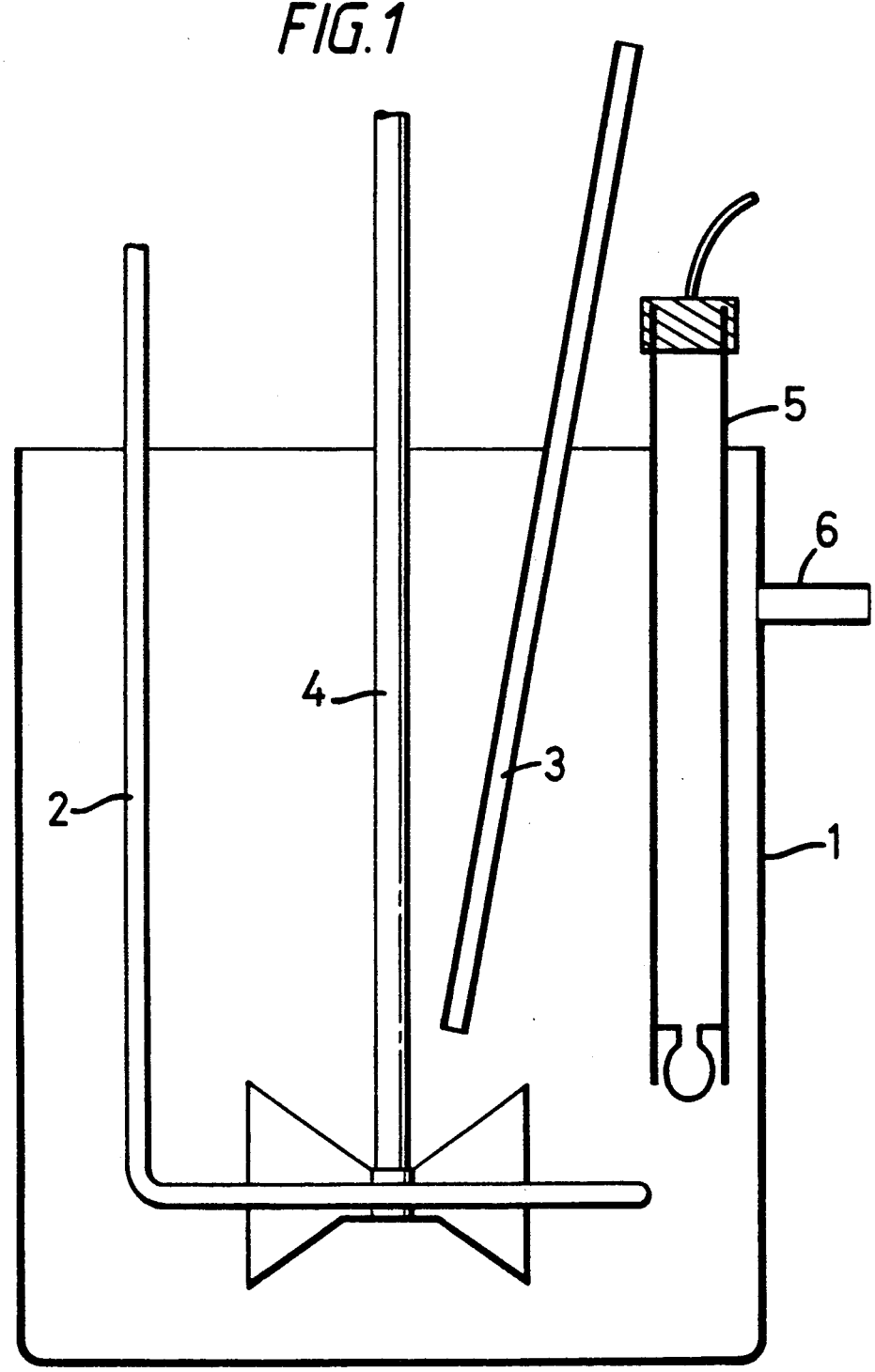

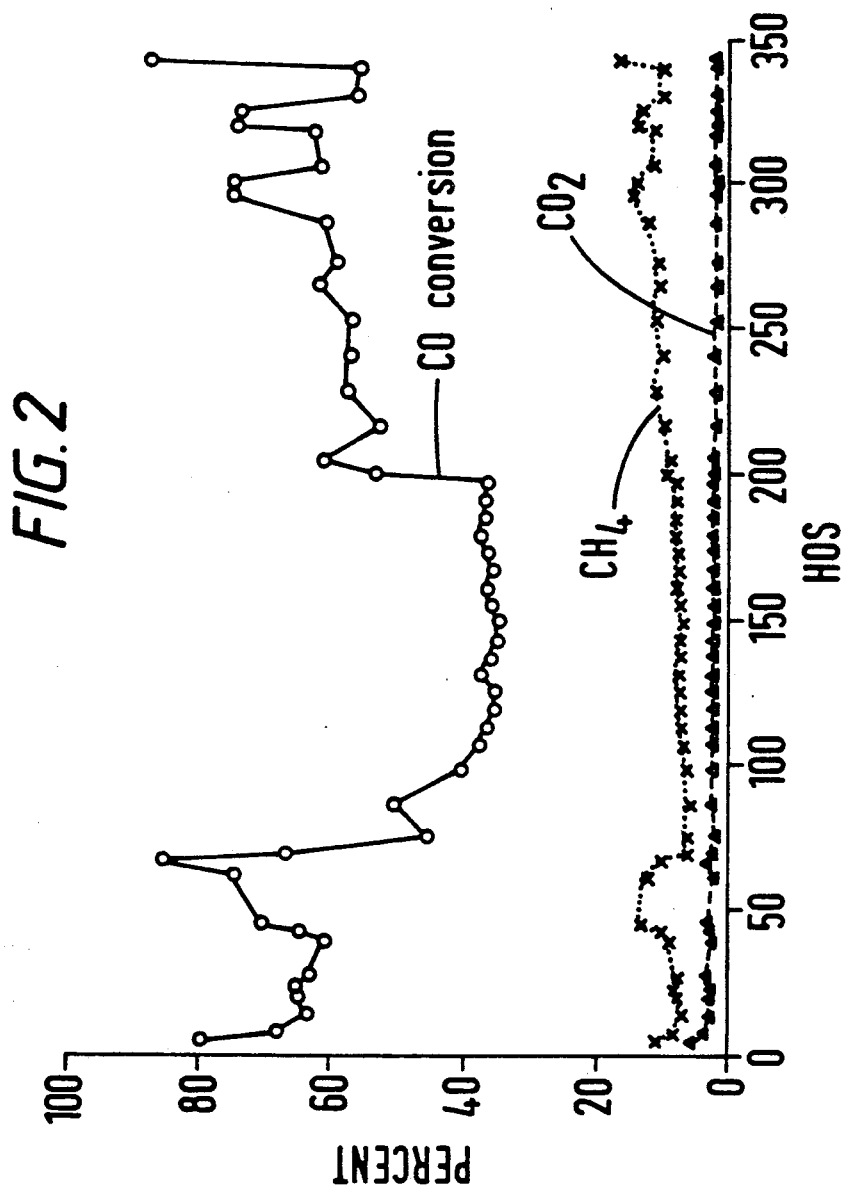

SYNGAS CONVERSION CATALYST, PRODUCTION AND USE THEREOF

This application is a continuation of application Ser. No. 07/647,693, filed Jan. 28, 1991, which is a continuation of Ser. No. 07/563,825, filed Aug. 3, 1990, which is a continuation of Ser. No. 07/308,106, filed Feb. 24, 1989, all abandoned, which is a division of Ser. No. 07/124,843, filed Aug. 5, 1987, now U.S. Ser. No. 4,826,803.

The present invention relates to a process for the production of an improved catalyst for use in the conversion of gaseous mixtures principally comprising carbon monoxide and hydrogen, hereinafter referred to as synthesis gas, to hydrocarbons of carbon number greater than one, in particular to aliphatic hydrocarbons in the gasoline boiling range, and to the use of the catalyst so-produced in the conversion of synthesis gas to the aforesaid hydrocarbons.

The conversion of synthesis gas to hydrocarbons by the Fischer-Tropsch process has been known for many years but the process has only achieved commercial significance in countries such as South Africa where unique economic factors prevail. The growing importance of alternative energy sources such as coal and natural gas has focussed renewed interest in the Fischer-Tropsch process as one of the more attractive direct and environmentally acceptable routes to high quality transportation fuels.

Of the Group VIII metals, ruthenium has lone been known to be one of the most active catalysts in the conversion of synthesis gas, the product, at moderate pressures and above, being high molecular weight paraffin waxes and, at low pressures, principally methane. Several recent patent publications, for example U.S. Pat. Nos. 4,042,614; 4,171,320; 4,206,134; 4,413,064 and 4,410,637 and GB-A-2119277, describe and claim the formation of different products from synthesis gas using catalysts containing ruthenium as an active component.

U.S. Pat. No. 4,042,614 describes a process for the selective synthesis of olefins from $C_2$ to $C_{10}$ chain length inclusive from synthesis gas using as catalyst ruthenium mon a titanium-containing oxide support, wherein said titanium-containing oxide support is selected from the group consisting of $TiO_2$, $ZrTiO_4$, $TiO_2$-carbon, $TiO_2$-$Al_2O_3$, $TiO_2$-$SiO_2$, alkaline earth titanates, rare earth titanates and mixtures thereof.

U.S. Pat. No. 4,171,320 describes a process for the synthesis of olefins of from $C_2$ to $C_5$ chain length inclusive from synthesis gas using as catalyst ruthenium on a support selected from the group consisting of $V_2O_3$, $Nb_2O_5$, $Ta_2O_5$, $Al_2O_3$-$V_2O_3$, $Al_2O_3$-$Nb_2O_5$, $Al_2O_3$-$Ta_2O_5$, $SiO_2$-$V_2O_3$, $SiO_2$-$Nb_2O_5$, $SiO_2$-$Ta_2O_5$, $V_2O_3$-carbon, $Nb_2O_5$-carbon, $Ta_2O_5$-carbon, alkaline earth-group VB oxides, alkali metal-Group VB oxides, Group IVB-Group VB oxides and mixtures thereof.

U.S. Pat. No. 4,206,134 describes a process for the enhanced synthesis of $C_2$-$C_4$ olefins with reduced production of methane from synthesis gas using as catalyst ruthenium on a managanese-containing oxide support, wherein said manganese-containing oxide support is selected from the group consisting of MnO, $Al_2O_3$-MnO, $SiO_2$-MnO, MnO-carbon, Group IVB-manganese oxide, Group VB-manganese oxides, rare earth-manganese oxides and mixtures thereof.

U.S. Pat. No. 4,413,064 describes a process for the conversion of synthesis gas to a product high in straight chain paraffins in the diesel fuel boiling range from synthesis gas utilising a catalyst consisting essentially of cobalt, thoria or lanthana and ruthenium on an alumina support wherein said alumina is gamma-alumina, eta-alumina or a mixture thereof, said catalyst being prepared by contacting finely divided alumina with
 (A) an aqueous impregnation solution of a cobalt salt, and
 (B) a nonaqueous, organic impregnation solution of a ruthenium salt and a salt of thorium or lanthanum.

U.S. Pat. No. 4,410,637 describes a process for the preparation of a hydrocarbon mixture consisting substantially of $C_5$-$C_{12}$ hydrocarbons from synthesis gas using a catalyst containing one or more of iron, nickel, cobalt, chromium and/or ruthenium and, as a carrier, magadite, a laminar crystalline silicate compound capable of absorbing metal ions or metal salts by intercalation.

The reaction of carbon monoxide and hydrogen on rare earth metal oxide catalysts is described in Chemical Communications, 1983, page 763/764 by Kieffer et al. Catalysts studied were Pd - $La_2O_3$ and Pd - $Dy_2O_3$, both of which were prepared by impregnation.

Finally, GB-A-2,119,277 describes a catalyst for the selective synthesis of olefins from a mixture of hydrogen and carbon monoxide or hydrogen and carbon dioxide comprising a ruthenium carbonyl compound deposited on a ceric oxide-containing support. In Example 3 there is disclosed a catalyst prepared by impregnating ceric oxide with an aqeous solution of $RuCl_3.3H_2O$ (ruthenium content 0.62% w/w). The impregnated catalyst when used in the conversion of synthesis gas (Run 9) produces an undesirably high methane yield (35.7%) and a low selectivity (1.6%) to desirable olefins.

In our European patent application publication No. 10169743 (BP Case No. 5890) there is described a process for the production of a composition for use after reductive activation as a catalyst in the conversion of synthesis gas to hydrocarbons of carbon number greater than one, which composition has the formula:

$$Ru_a A_b CeO_x \qquad (I)$$

wherein
 A is an alkali metal,
 x is a n umber such that the valence requirements of the other elements for oxygen is satisfied,
 a is greater than zero and less than 1% w/w, based on the total weight of the composition,
 b is in the range from zero to 10% w/w. based on the total weight of the composition, and
 Ce and O constitute the remainder of the composition,
which process comprises the steps of:
 (A) bringing together in solution soluble salts of the metals ruthenium and cerium and a precipitant comprising a carbonate and/or a bicarbonate and/or a hydroxide of an alkali metal or ammonium under conditions whereby there is formed a precipitate comprising ruthenium and cerium in the form of compounds thermally decomposable to their oxides, and
 (B) recovering the precipitate obtained in step (A).

In the embodiment of the invention specifically described therein, an aqueous solution of the precipitant is added to an aqueous solution of water soluble salts of the metals.

We have now surprisingly found that very active and long-lived catalysts are obtained when a solution or solutions of compounds of ruthenium and cerium, and optionally also an alkali metal compound, are added to a solution of the precipitant, which order of addition is the reverse of that previously described.

Accordingly, the present invention provides a process for the production of a composition for use after reductive activation as a catalyst in the conversion of synthesis gas to hydrocarbons of carbon number greater than one, which composition has the formula:

$$Ru_a A_b Ce O_x \tag{I}$$

wherein
A is an alkali metal,
x is a number such that the valence requirement of the other elements for oxygen is satisfied,
a is greater than zero and less than 5% w/w, based on the total weight of the composition,
b is in the range from zero to 10% w/w, based on the total weight of the composition, and
Ce and O constitute the remainder of the composition, which comprises the steps of:
(A) adding a solution or solutions of soluble compounds of the metals rutheniuim and cerium, and optionally also an alkali metal compound, to a solution of a precipitant comprising a carbonate and/or a bicarbonate and/or a hydroxide of an alkali metal or ammonium under conditions whereby there is formed a precipitate comprising ruthenium and cerium, and optionally also an alkali metal, in the form of compounds thermally decomposable to the metals and/or their oxides, and
(B) recovering the precipitate obtained in step (A).

Preferably a in the formula (1) is less than 1% w/w.

In the formula (I) A is an alkali metal, which is preferably potassium. Preferably the amount b of alkali metal is greater than zero and up to 5% w/w, even more preferably up to 2% w/w.

As regards step (A) of the process, a solution or solutions of soluble compounds of the metals ruthenium and cerium, and optionally also an alkali metal, is added to a solution of a precipitant comprising a carbonate and/or a bicarbonate and/or a hydroxide of an alkali metal or ammonium under conditions whereby there is formed a precipitate comprising ruthenium and cerium, and optionally also an alkali metal, in the form of compounds thermally decomposable to the metals and/or their oxides.

In a preferred embodiment of the process step (A) may be operated continuously by feeding simultaneously to a precipitation zone and mixing therein a solution or solutions of soluble compounds of the metals ruthenium and cerium, and optionally also an alkali metal, and a solution of the precipitant under conditions whereby there is formed a precipitate comprising ruthenium and cerium, and optionally also an alkali metal, in the form of compounds thermally decomposable to their oxides. The precipitation zone may suitably take the form of a vessel provided with means for separately introducing a solution of soluble compounds of ruthenium and cerium, and optionally also alkali metal, and a solution of the precipitant, the means for separately introducing the solutions being so arranged as to achieve mixing of the solutions, agitation means, pH measuring means and means for continuously withdrawing the suspended precipitate, for example an overflow pipe.

Suitably the solution or solutions employed may be aqueous solutions. The compounds of ruthenium and cerium, and optionally also the alkali metal compound, may be contained in separate solutions and added to the precipitant solution in any order or they may be contained in a single solution and thereby added together to the precipitant.

Whilst any soluble compound of ruthenium and cerium may be employed, it will usually be found convenient to use ruthenium in the form of the chloride because this is a commercially available form and cerium in the form of the nitrate, for example cerous nitrate. Commercially available cerous nitrate, which contains rare earth metals other than cerium, may be employed if desired.

The precipitant in step (A) may be a carbonate and/or a bicarbonate and/or a hydroxide of an alkali metal. Instead of using a pre-formed carbonate or bicarbonate it is possible to use the precursors of these salts, for example a water soluble salt and carbon dioxide. Alternatively, urea, which is thermally decomposable to carbon dioxide and ammonia, may be used. In any event, b in the aforesaid formula (I) will have a value greater than zero, which value may be adjusted if desired by washing or addition of further alkali metal compound. Alternatively, ammonium carbonate and/or bicarbonate and/or hydroxide may be employed as the precipitant, in which case the value of b in the catalyst asinitially produced will be zero, though this value may subsequently be adjusted if desired by addition of alkali metal. Preferably ammonium bicarbonate, optionally mixed with an alkali metal bicarbonate, for example potassium bicarbonate, is used as the precipitant.

Suitably the soluble compounds of the metals ruthenium and cerium may be brought together at a temperature in the range from 0° to 100° C. In one preferred embodiment of the invention the temperature is suitably in the range from 60° to 100° C., preferably from 80° to 100° C. In another preferred embodiment the temperature is suitably below 50° C., preferably below 30° C., for example ambient temperature.

Precipitation may suitably be effected at a pH greater than about 6, preferably in the range from 6 to 10. Preferably the pH is substantially constant within the aforesaid range throughout the precipitation step. A substantially constant pH may suitably be achieved by using a large excess of the precipitant, for example about seven times the theoretical stoichiometric amount required for complete precipitation. Alternatively, a suitable buffer may be employed.

In continuous operation of step (A) the solutions are preferably fed at a relative rate such as to achieve a substantially constant pH within the aforesaid ranges. In order to achieve a substantially constant pH it may be desirable to further feed a solution of an inorganic base, for example aqueous ammonia.

In order to improve the homogeneity of the catalyst it is preferred to agitate the mixture during precipitation, suitably by mechanical stirring.

The amounts of the rutheniuim and cerium compounds and precipitant employed should be such as to satisfy the stoichiometric relationships in the formula (I). Alternatively, the alkali metal content of the composition may be supplemented by further addition thereof, or reduced, for example by washing, at any subsequent point in the preparative process.

In step (B) the precipitate obtained in step (A) is recovered. This may suitably be accomplished by filtration but other methods for separating solids from liquids, for example centrifugation, may be employed. After recovery it is preferred to wash the precipitate, suitably with water, so as to remove unwanted residual soluble matter. It is also preferred to dry the precipitate, suitably at a temperature below 180° C., for example about 100° to 150° C. It is possible that some thermal decomposition may occur in the drying step.

Thermally decomposable compounds comprised in the precipitate recovered in step (B) are preferably further thermally decomposed in a discrete step (C). This may suitably be accomplished by heating the precipitate, suitably in a non-reducing atmosphere, for example a stream of inert gas, such as nitrogen, at a temperature suitably in the range from 150° to 600° C.

In order to convert the composition of formula (I) into a catalyst for use in the conversion of syngas to hydrocarbons having a carbon number greater than 1, it is generally necessary to reductively activate the composition, suitably by contact at elevated temperature with a reducing gas, for example hydrogen, carbon monoxide or mixtures thereof. A suitable reducing gas is for example hydrogen which may be diluted with an inert gas such as argon. Typically, the conditions employed may suitably be a pressure in the range from 1 to 100 bar and a temperature in the range from 150° to 600° C. for a period of up to 24 hours or longer. Reductive activation may be effected as a discrete step prior to use as a catalyst for the conversion of synthesis gas or it may be incorporated as preliminary step into the synthesis gas conversion process, preferably the latter.

Those skilled in the art will readily appreciate that it may be possible to combine the thermal decomposition step and the reductive activation step into a single step under certain circumstances.

It is believed that coprecipitated catalysts differ fundamentally from impregnated catalysts and that this difference is reflected in their catalytic performance.

The present invention also provides a process for the production of hydrocarbons having a carbon number greater than one from synthesis gas which process comprises contacting synthesis gas with a catalyst comprising a reductively activated composition having the formula (I) produced by the process of claim 1 at a temperature in the range from 190° to 400° C. and a pressure in the range from about 1 bar to 100 bar.

Reductive activation of the composition of formula (I) may be conducted either as a separate step outside the syngas conversion reactor, as a discrete step within the syngas conversion reactor prior to syngas conversion or within the syngas conversion reactor under syngas conversion conditions.

We have noted that benefits can arise from periodically treating the catalyst with hydrogen. This may suitably be accomplished by shutting off the carbon monoxide feed from time to time during the process.

As is well known in the art synthesis gas principally comprises carbon monoxide and hydrogen and possibly also minor amounts of carbon dioxide, nitrogen and other inert gases depending upon its origin and degree of purity. Methods for preparing synthesis gas are established in the art and usually involve the partial oxidation of a carbonaceous substance, e.g. coal. Alternatively, synthesis gas may be prepared, for example by the catalytic steam reforming of methane. For the purpose of the present invention the carbon monoxide to hydrogen ratio may suitably be in the range from 2:1 to 1:6. Whilst the ratio of the carbon monoxide to hydrogen in the synthesis gas produced by the aforesaid processes may differ from these ranges, it may be altered appropriately by the addition of either carbon monoxide or hydrogen, or may be adjusted by the so-called shift reaction well known to those skilled in the art.

In a modification of the process for the production of hydrocarbons, there may be combined with the catalyst an inert material, for example silica.

In a preferred embodiment, the catalyst may be combined with an acidic component, for example either a zeolite or a pillared clay.

The zeolite or pillared clay may be either physically admixed with the composition to form an intimately mixed bed or may be separate therefrom, for example in the form of a split bed, the zeolite or pillared clay forming one portion of the bed and the catalyst another. In the case of a physical admixture, the zeolite or pillared clay may be mixed with the composition either before or after reductive activation. Alternatively, the coprecipitation (step A) in the process for producing the composition of formula (I) may be performed in the presence of the zeolite or pillared clay, particularly when the precipitant is ammonium carbonate and/or bicarbonate and/or hydroxide.

A suitable zeolite is an MFI-type zeolite, for example ZSM-5 as described in U.S. Pat. No. 3,702,886, though other suitable high silica crystalline alumino- or gallo-silicate zeolites may be employed.

Suitable pillared clays are described for example in GB-A-2,059,408, U.S. Pat. No. 4,216,188, U.S. Pat. No. 4,248,739, U.S. Pat. No. 4,515,901 and U.S. Pat. No. 4,367,163. A particularly suitable pillared clay is the silylated pillared clay described in our copending EP-A-0150898 (BP Case No. 6035). The aforesaid patent publications are incorporated by reference herein.

The temperature is preferably in the range from 250° to 350° C. and the pressure is preferably in the range from 10 to 50 bars. The GHSV may suitably be in the range from 100 to 20,000h$^{-1}$.

The process may be carried out batchwise or continuously in a fixed bed, fluidised bed, moving bed or slurry phase reactor.

In addition to their high activities and long lifetimes, catalysts produced by the process of the present invention provide low selectivities to methane and carbon dioxide, thereby minimising carbon wastage in the form of undesirable by-products.

The invention will now be further illustrated by the following Examples.

A. CATALYST PREPARATION

Example 1

$RuCl_3(H_2O)_x(0.3974$ g; 1.52 mmoles) dissolved in distilled water (100 cm$^3$) was added dropwise to a vigorously stirred solution of $Ce(NO_3)_3.(H_2O)_6(75.40$ g; 173.64 mmoles) made up to 750 cm$^3$ with distilled water. A solution of $KNO_3(1.1421$ g; 11.30 mmoles) in distilled water (50 cm$^3$) was then added dropwise to the aqueous ruthenium chloride/cerous nitrate with stirring. The solution containing rutheniuim/cerium and potassium was added to freshly prepared aqueous $NH_4HCO_3(299.7$ g; 3.79 mmoles) made up to 2500 cm$^3$ with distilled water over ca. 1 hour. The pH of the alkali was constant at 8.7–8.8 throughout the precipitation. Stirring was continued for 0.25 h after all of the reagents were added and the mixture was vacuum filtered to yield a light grey sludge and a light yellow filtrate. The sludge was vigorously stirred with distilled water (3000 cm$^3$) for 0.25 h and then vacuum filtered. This procedure was repeated three times and the grey solid was partially dried on the vacuum filter before final drying in a vacuum oven (116° C., 17 mm Hg, ca 24 h). The dried solid (ca 25 g) was ground to a fine powder and then pressed in a 3.5 cm die at 10–11 tons. The pressed solid was crushed and sieved to 500–1400 μm. A portion (ca 20 g) was given the following heat treatments:

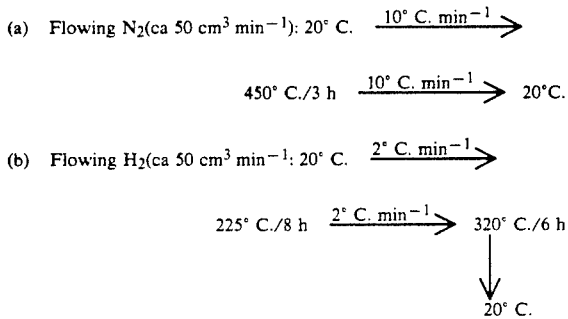

The heat-treated catalyst was exposed to air and stored in air in screw-top jars.

Example 2

The procedure of Example 1 was repeated except that the pH control during precipitation was inferior to that of Example 1, the pH varying from 8.40–8.65.

Example 3

A similar procedure to that of Example 1 was used except that approx. three times the quantity of reagents was used to yield 64.70 g of product gel. The RuCl$_3$/Ce(NO$_3$)$_3$ solution was added to the aqueous NH$_4$HCO$_3$ solution at the rate of 50 cm$^3$min$^{-1}$. The addition of reagents was therefore completed in approx. the same time period (69 minutes) as the smaller scale preparations of Examples 1 and 2. The pH of the aqueous NH$_4$HCO$_3$ rose from 8.16 to 8.68 during the preparation.

Example 4

Continuous Precipitation with NH$_4$HCO$_3$

In this Example the apparatus illustrated in FIG. 1 was employed. With reference to FIG. 1 is a stainless steel constant head mixing vessel, 2 is a precipitant delivery ring, 3 is a pipe for delivery of solution containing metals to be precipitated, 4 is a paddle stirrer, 5 is a pH electrode and 6 is an overflow pipe.

Solution A

RuCl$_3$(H$_2$O)$_3$ (12.085 g; 46.23 mmoles) was dissolved in distilled water (0.40 liter) and added dropwise to a vigorously stirred solution of Ce(NO$_3$)$_3$(H$_2$O)$_6$ (303 g; 0/698 moles) made up to 3 liters with distilled water. A solution of KNO$_3$ (4.700 g; 46.24 m moles) in distilled water (0.20 l) was then added dropwise to the aqueous ruthenium chloride/cerous nitrate solution with stirring. This solution is hereinafter referred to as solution A.

Solution B

NH$_4$HCO$_3$ (1.20 kg; 15.18 moles) was dissolved in 10 liters of distilled water. This solution is hereinafter referred to as solution B.

Method

With reference to FIG. 1, solution A was fed through pipe 3 and solution B was fed simultaneously through the precipitant delivery ring 2 to the constant head mixing vessel 1 via peristatic pumps (not shown) at a flow rate ratio sufficient to control the pH in the mixing vessel 1 as measured by the pH electrode 5 between 8.0 and 8.7. Efficient mixing of the solution A and B was received by rapid rotation of the paddle stirrer 4. The suspended precipitate was constantly bled off via the overflow pipe 6 and filtered on three 5 liter Buchner Funnel/Flasks to yield a light grey solid and a light yellow filtrate. The individual solids were sucked dry on the filter over ca. 2 hours and were left for 17 hours in air. The solids showed some signs of darkening during drying. The solids from the three Buchner Funnels were combined to yield 916.3 g in total.

The damp cake was split into two portions C(279.3 g) and D(630 g).

Portion D was vigorously stirred with distilled water (2 liters) and filtered. This washing procedure was repeated twice more and finally the solid was vacuum dried (100° C., 17 mm Hg, 17 h) to yield 60.75 g of dried gel.

The dried gel was then pressed and heat treated in an identical manner to that described in Example 1.

Example 5

Continuous Precipitation with KHCO$_3$

The procedure described in Example 4 was repeated except that NH$_4$HCO$_3$ was replaced by KHCO$_3$ and the following quantities of reagents were used:

Solution A (i) RuCl$_3$(H$_2$O)$_3$ [155 g; 5.93 moles in distilled water (0.040l)], (ii) KNO$_3$ [4.667 g; 46.17 mmoles in distilled water (0.20l)], (iii) Ce(NO$_3$)$_3$(H$_2$O)$_6$ [302.86 g; 0.697 mole in distilled water (10l)].

Solution (i) was added to solution (iii). Solution (ii) was added to the mixed solution (i) and (iii).

Solution B

KHCO$_3$ [1520.9 g; 15.19 moles in distilled water (10l)].

The co-precipitation was effected at a pH between 7.70 and 7.90.

The precipitated solid was vacuum filtered to yield a dense metallic silver sludge.

The dried solid was washed with (i) 10l, (ii) 12l (iii) 10l of distilled water before drying at 110° C. in air for 17 hours.

The dried solid was pressed and heat treated in a manner identical to that described in Example 1.

Example 6

Larger Scale Continuous Precipitation with $NH_4HCO_3$

The procedure described in Example 4 was repeated using the following quantities of reagents:

Solution A (i) $RuCl_3(H_2O)_3$ [43.46 g; 166.24 mmoles in distilled water (11.21)],
(ii) $KNO_3$ [130.66 g; 1292.47 mmoles in distilled water (5.61)],
(iii) $Ce(NO_3)_3(H_2O)_6$ [8.48 kg; 19.53 moles in distilled water (841)].

Solution (i) was added to solution (iii). Solution (ii) was added to the mixed solution (i) and (iii).

Solution B $NH_4HCO_3$ [4.80 kg; 60.72 moles in distilled water (401)]. The pH of the coprecipitation was adjusted to 8.50 using 0.880 aqueous ammonia.

The light grey precipitate produced by the coprecipitation was vacuum filtered and washed three times with 50-55l distilled water. The damp cake so-produced was dried at 110° C. in air for 30 hours.

The dried gel was sieved to less than 1 cm and roasted in nitrogen using the following procedure.

Flowing $N_2(31\ min^{-1})/20°$ C. $\xrightarrow{3\ h}$ 450° C./6 h $\xrightarrow{14\ h}$ 20° C.
7 kg gel The nitrogen-roasted gel was then mixed with distilled water (0.61 $kg^{-1}$) in a 'Z' blade mixer. Finally, it was dried at 30° C. in air for 30 h.

The powder was crushed and sieved to less than 1 mm and was then dry mixed with stearic acid (2 g acid to 100 g dry gel).

The mixture was then pelleted using a Manesty B3B 16 station multiple punch tablet maker to yield 4.8 mm diameter×4.0 mm long cylindrical pellets. These pellets were crushed and sieved to 250-500 μm before testing.

B. CATALYST TESTING

Example 7

(i) Procedure

4 $cm^3$ of catalyst prepared in Example 1 were mixed with 6 $cm^3$ of crushed ceramic beads of the same particle size and charged to a fixed bed reactor. It was reduced for 16 h at 225° C. under 75 $cm^3\ min^{-1}$ $H_2$ at atmospheric pressure. It was then pressurised under syngas (2:1 $H_2$:CO) to 30 barg and heated to 305°-315° C. (bed) over 2 h. At this point the CO flow was stopped for 2 h. CO was then readmitted and the wall temperature reduced to give a bed temperature of 295°-300° C. Conditions were then kept constant until a steady state was acheived, after which process parameters were altered as desired.

(ii) Results

Data obtained at various times on stream and at different temperatures are given in Table 1. The run was continued for 2200 hours during which time the bed temperature was varied between 300+ and 314° C. corresponding to CO conversions ranging between 37% and 88%. The data derived in terms of CO conversion, $CH_4$ selectivity and $CO_2$ selectivity over the initial 350 hours of the test are plotted in FIG. 2.

It can be seen from FIG. 2 that the catalyst stabilised after about 100 HOS and $CO_2$ selectivity was uniformly low throughout the test. Methane selectivity was uniformly low at constant conversion. Moreover, the catalyst was reproducible in the sense that similar conversions were obtained at similar temperatures at different times on stream with intervening temperature changes.

The catalyst maintained its performance during the period 350 HOS to 2200 HOS.

Example 8

(i) Procedure

Using the catalyst produced in Example 4 in place of the catalyst produced in Example 1 the procedure of Example 7 was repeated except that the catalyst was reduced for 6 h at 305° C. (30 bar $H_2$, 111 $cm^3\ min^{-1}$). At 47 HOS the catalyst was given a hydrogen treatment by stopping the CO flow for one hour.

(ii) Results

The results are presented in Table 2.

It can be seen from the Table that at similar CO conversions the treatment with hydrogen after 47 HOS leads to very much lower methane selectivity and a reduced $CO_2$ selectivity.

Example 9

(i) Procedure

Using the catalyst produced in Example 5 in place of the catalyst produced in Example 1 the procedure of Example 7 was repeated except that the catalyst was reduced for 6 h at 305° C. (30 bar $H_2$, 111 $cm^3\ min^{-1}$).

(ii) Results

The results are presented in Table 3.

It can be seen from Table 1 that the methane selectivity is very low. A particularly attractive result is that obtained at 81.47% conversion (17 HOS) with a methane selectivity of only 10.66% and a $CO_2$ selectivity of only 3.59%.

Example 10

(i) Procedure

2 $cm^3$ of the catalyst produced in Example 6 was reduced in flowing hydrogen (83.4 $cm^3\ min^{-1}$) using the following temperature regimes:

100° C. for 1 hour, followed by 200° C. for 1 hour and then 300° C. for 16 hours followed by cooling to 200° C.

The catalyst was then exposed to synthesis gas ($H_2$:CO=2:1) (83.4 $cm^3\ min^{-1}$ total flow) and equilibrated for 1 hour. The temperature was adjusted to 250° C. for ca. 0.5 h and then increased to 270° C. before increasing to 290° C. in 10° C. steps and finally to the operating temperature (ca. 300° C.) in 1° C. steps.

The results are presented in Table 4.

The results presented in the Table demonstrate the flexibility of the catalyst and in particular that high CO conversions are achieved at low $CH_4$ and $CO_2$ selectivities over 500 HOS.

TABLE 1

| HOS | Bed Temperature (°C.) | CO Conversion (%) | Carbon Molar Selectivity (%) | | | | | | | Productivity (g/l/h) | |
|---|---|---|---|---|---|---|---|---|---|---|---|
| | | | $C_1$ | $C_2$ | $C_3$ | $C_4$ | $C_5^+$ | $CO_2$ | Oxygenates | $C_2^+$ | $C_5^+$ |
| 197 | 300 | 37.1 | 8.3 | 3.2 | 11.2 | 12.5 | 62.2 | 2.3 | 0.3 | 166 | 120 |
| 330 | 305 | 56.6 | 10.7 | 2.8 | 8.9 | 10.0 | 64.5 | 2.1 | 1.0 | 233 | 180* |
| 320 | 309 | 74.9 | 14.5 | 3.0 | 7.0 | 6.3 | 66.2 | 2.2 | 0.8 | 292 | 242* |
| 343 | 314 | 88.0 | 17.0 | 2.8 | 11.9 | 11.7 | 53.8 | 2.4 | 0.4 | 373 | 259 |

*Suspected loss of $C_3$ and $C_4$ hydrocarbons from liquid product

TABLE 2

| HOS | Bed Temperature (°C.) | CO Conversion (%) | Carbon Molar Selectivity (%) | | | | | | | Productivity (g/catalyst/h) | |
|---|---|---|---|---|---|---|---|---|---|---|---|
| | | | $C_1$ | $C_2$ | $C_3$ | $C_4$ | $C_5^+$ | $CO_2$ | Oxygenates | $C_3^+$ | $C_5^+$ |
| 8.5 | 307 | 79.9 | 11.7 | 2.7 | 6.2 | 6.0 | 67.0 | 4.8 | 1.6 | 295 | 250 |
| 14.5 | 307 | 79.7 | 12.8 | 3.0 | 6.5 | 6.3 | 65.3 | 4.7 | 1.5 | 300 | 251 |
| 20.5 | 307 | 79.5 | 14.9 | 3.4 | 6.1 | 6.3 | 63.5 | 4.5 | 1.5 | 302 | 252 |
| 27.0 | 306 | 75.6 | 14.7 | 3.3 | 6.5 | 6.6 | 63.3 | 4.2 | 1.4 | 289 | 239 |
| 39.0 | 306 | 74.7 | 15.0 | 3.4 | 7.2 | 6.9 | 62.1 | 4.0 | 1.4 | 291 | 237 |
| | | | | | $H_2$ TREATMENT | | | | | | |
| 121.0 | 303 | 73.2 | 7.7 | 2.5 | 7.2 | 7.1 | 70.8 | 3.4 | 1.3 | 315 | 262 |
| 134.0 | 300 | 60.3 | 7.4 | 2.4 | 9.8 | 10.5 | 65.4 | 3.2 | 1.3 | 263 | 201 |
| 143.0 | 300 | 60.1 | 7.4 | 2.7 | 9.3 | 10.7 | 65.5 | 2.9 | 1.6 | 261 | 200 |

TABLE 3

| HOS | Bed Temperature (°C.) | CO Conversion (%) | Carbon Molar Selectivity (%) | | | | | | | Productivity (g/l/h) | |
|---|---|---|---|---|---|---|---|---|---|---|---|
| | | | $C_1$ | $C_2$ | $C_3$ | $C_4$ | $C_5^+$ | $CO_2$ | Oxygenates | $C_3^+$ | $C_5^+$ |
| 29 | 305 | 51.0 | 5.6 | 2.6 | 8.8 | 9.6 | 68.9 | 3.1 | 1.4 | 237 | 187 |
| 38 | 305 | 44.9 | 5.5 | 3.0 | 9.7 | 12.2 | 66.2 | 2.5 | 0.9 | 211 | 158 |
| 59 | 305 | 43.2 | 6.0 | 3.0 | 9.8 | 12.2 | 65.4 | 2.6 | 1.0 | 201 | 150 |
| 77 | 305 | 43.2 | 6.2 | 3.1 | 9.9 | 12.2 | 65.2 | 2.4 | 1.0 | 200 | 150 |
| 79 | 310 | 53.6 | 6.1 | 3.1 | 9.0 | 10.2 | 67.7 | 2.9 | 1.0 | 248 | 193 |
| 87 | 310 | 49.0 | 6.6 | 3.2 | 9.9 | 11.4 | 65.0 | 2.9 | 1.0 | 225 | 169 |
| 99 | 310 | 52.3 | 6.6 | 3.1 | 9.2 | 10.5 | 66.9 | 2.7 | 1.0 | 241 | 186 |
| 107 | 310 | 49.8 | 6.8 | 3.1 | 9.5 | 10.8 | 65.9 | 2.9 | 1.1 | 228 | 175 |
| 110 | 310 | 47.0 | 7.6 | 3.0 | 9.2 | 9.1 | 67.3 | 2.9 | 1.2 | 214 | 168 |
| 120 | 310 | 54.4 | 7.1 | 3.1 | 9.9 | 10.5 | 65.6 | 2.8 | 1.0 | 249 | 190 |
| 131 | 310 | 53.3 | 7.2 | 3.2 | 9.5 | 10.3 | 66.2 | 2.7 | 1.0 | 244 | 188 |
| 135 | 315 | 72.4 | 11.5 | 3.0 | 5.3 | 3.6 | 71.9 | 3.9 | 0.9 | 311 | 277 |
| 140 | 315 | 65.2 | 8.6 | 3.1 | 8.3 | 7.8 | 68.1 | 3.2 | 0.9 | 292 | 236 |
| 146 | 315 | 66.4 | 7.8 | 2.7 | 8.1 | 8.6 | 69.0 | 2.9 | 0.9 | 302 | 244 |
| 159 | 315 | 69.4 | 7.3 | 2.9 | 7.7 | 8.2 | 71.1 | 2.7 | 0.3 | 321 | 262 |
| 172 | 315 | 67.4 | 7.8 | 2.8 | 7.9 | 8.6 | 70.0 | 2.6 | 0.3 | 310 | 251 |
| 183 | 320 | 81.5 | 10.7 | 3.6 | 7.1 | 6.8 | 68.0 | 3.6 | 0.3 | 355 | 295 |
| 196 | 320 | 78.4 | 12.0 | 2.8 | 6.0 | 6.2 | 69.4 | 3.3 | 0.3 | 340 | 289 |
| 202 | 320 | 75.1 | 12.7 | 2.8 | 6.4 | 6.0 | 68.4 | 3.4 | 0.3 | 323 | 273 |
| 210 | 320 | 75.9 | 12.6 | 3.0 | 6.4 | 5.8 | 68.5 | 3.4 | 0.2 | 326 | 277 |
| 222 | 320 | 69.1 | 13.5 | 3.2 | 7.5 | 7.2 | 64.9 | 3.5 | 0.2 | 293 | 239 |
| 240 | 320 | 64.6 | 14.2 | 3.2 | 7.4 | 7.2 | 64.0 | 3.6 | 0.3 | 271 | 220 |
| 274 | 320 | 49.1 | 13.6 | 3.9 | 10.4 | 12.4 | 54.7 | 4.8 | 0.3 | 202 | 143 |
| 304 | 320 | 79.6 | 14.4 | | | | | | | | |
| 308 | 320 | 83.7 | 12.5 | | | | | | | | |
| 314 | 320 | 76.8 | 11.4 | | | | | | | | |
| 320 | 320 | 74.1 | 11.7 | | | | | | | | |
| 325 | 320 | 71.8 | 12.0 | | | | | | | | |

TABLE 4

| HOS | GHSV ($h^{-1}$) | Dilution (Cat:Diluent) | Temp (°C.) | CO Conversion (%) | Carbon Molar Selectivity (%) | | | | | | Productivity ($kgm^{-3} cat.h^{-1}$) | |
|---|---|---|---|---|---|---|---|---|---|---|---|---|
| | | | | | $CH_4$ | $CO_2$ | $C_2$ | $C_3^+$ | $C_5^+$ | Oxygenates | $C_3^+$ | $C_5^+$ |
| 23 | 2500 | — | 295 | 52.5 | 9.7 | 3.4 | 2.7 | 84.2 | 64.3 | — | 240.7 | 183.8 |
| 65 | 2500 | — | 294 | 53.0 | 10.4 | 3.1 | 3.1 | 83.4 | 62.0 | — | 240.3 | 178.8 |
| 76 | 2500 | — | 296 | 65.2 | 6.9 | 2.4 | 2.0 | 88.7 | 72.9 | — | 314.5 | 258.5 |
| 88 | 2500 | — | 293 | 56.2 | 7.8 | 2.3 | 2.3 | 87.6 | 69.7 | — | 268.1 | 213.4 |
| 94 | 2500 | — | 297 | 65.5 | 8.0 | 2.3 | 1.7 | 87.9 | 70.2 | — | 313.2 | 250.2 |
| 112 | 2500 | — | 296 | 63.3 | 8.7 | 2.5 | 2.5 | 86.2 | 67.5 | — | 297.7 | 232.7 |
| 136 | 2500 | — | 296 | 60.5 | 8.0 | 2.3 | 2.4 | 87.4 | 68.9 | — | 287.9 | 227.0 |
| 162 | 2500 | — | 304 | 83.7 | 7.9 | 2.3 | 2.0 | 87.8 | 75.3 | — | 400.0 | 343.3 |
| 185.8 | 2500 | — | 304 | 82.0 | 8.3 | 2.2 | 2.1 | 87.4 | 73.7 | — | 390.1 | 328.7 |
| 211.8 | 2500 | — | 304 | 79.4 | 8.6 | 2.6 | 2.2 | 86.5 | 72.9 | — | 373.8 | 315.2 |
| 233.8 | 2500 | — | 304 | 79.9 | 8.1 | 2.4 | 2.1 | 87.5 | 73.1 | — | 380.5 | 318.0 |
| 256 | 2500 | — | 303 | 76.4 | 8.2 | 2.4 | 2.2 | 87.2 | 72.3 | — | 362.7 | 300.5 |
| 280 | 2500 | — | 305 | 79.5 | 8.9 | 2.6 | 2.3 | 86.3 | 72.5 | — | 373.7 | 313.6 |

TABLE 4-continued

| HOS | GHSV ($h^{-1}$) | Dilution (Cat:Diluent) | Temp (°C.) | CO Conversion (%) | Carbon Molar Selectivity (%) | | | | | | Productivity ($kgm^{-3}\ cat.h^{-1}$) | |
|---|---|---|---|---|---|---|---|---|---|---|---|---|
| | | | | | $CH_4$ | $CO_2$ | $C_2$ | $C_3^+$ | $C_5^+$ | Oxygenates | $C_3^-$ | $C_5^-$ |
| 3044 | 2500 | — | 305 | 81.1 | 7.4 | 2.1 | 1.9 | 88.6 | 75.0 | — | 391.3 | 331.3 |
| 330 | 2500 | — | 306 | 79.3 | 7.6 | 2.1 | 2.0 | 88.3 | 74.8 | — | 380.7 | 322.5 |
| 361 | 2500 | — | 306 | 78.0 | 7.5 | 2.3 | 1.9 | 88.3 | 73.9 | — | 374.6 | 313.6 |
| 401 | 2500 | — | 304 | 76.8 | 7.5 | 2.1 | 2.0 | 88.3 | 73.4 | — | 368.9 | 306.5 |
| 425 | 2500 | — | 304 | 74.4 | 7.4 | 2.1 | 1.9 | 88.6 | 73.6 | — | 358.7 | 298.1 |
| 449 | 2500 | — | 306 | 74.6 | 7.7 | 2.2 | 2.0 | 88.1 | 73.3 | — | 357.7 | 297.5 |
| 472 | 2500 | — | 310 | 79.8 | 8.5 | 2.4 | 2.1 | 86.9 | 72.8 | — | 377.3 | 316.1 |
| 499 | 2500 | — | 309 | 78.8 | 8.7 | 2.5 | 2.1 | 86.7 | 72.0 | — | 371.7 | 308.8 |

We claim:

1. A process for the production of hydrocarbons having a carbon number greater than one from synthesis gas comprising hydrogen and carbon monoxide which process comprises contacting synthesis gas at a temperature in the range from 190° to 400° C. and a pressure in the range from about 1 bar to 100 bar with a catalyst comprising a reductively activated composition having the formula $$Ru_a A_b CeO_x \qquad (I)$$

wherein

A is an alkali metal, x is a number such that the valence requirements of the other elements for oxygen is satisfied, a is greater than zero and less than 5% w/w, based on the total weight of the composition, b is in the range from zero to 10% w/w, based on the total weight of the composition, and Ce and O constitute the remainder of the composition, which composition is prepared by the steps of:

(A) adding a solution or solutions of soluble compounds of the metals ruthenium and cerium, and optionally also an alkali metal compound, to a solution of a precipitant comprising a carbonate and/or a bicarbonate and/or a hydroxide of an alkali metal or ammonium under conditions whereby there is formed a precipitate comprising ruthenium and cerium, and optionally also an alkali metal, in the form of compounds thermally decomposable to the metals and/or their oxides, and (B) recovering the precipitate obtained in step (A).

2. A process according to claim 1 wherein a in the formula (I) has a value less than 1% w/w.

3. A process according to claim 1 wherein the composition having the formula (I) is reductively activated in a preliminary step in the synthesis gas conversion process.

4. A process according to claim 3 wherein the catalyst is periodically treated with hydrogen.

* * * * *

UNITED STATES PATENT AND TRADEMARK OFFICE
CERTIFICATE OF CORRECTION

PATENT NO. : 5,118,891
DATED      : June 2, 1992
INVENTOR(S) : GRAHAM BUTLER and MALCOLM P. HEYWARD It is certified that error appears in the above-identified patent and that said Letters Patent is hereby corrected as shown below:

Col. 1, l. 44, should read "on a titanium"

Col. 5, l. 32, after "as" and before "preliminary" insert --a--

Col. 7, l. 63, should read "0.698 moles)"

Col. 8, l. 63, after "121" and before (iii) insert --and--

Col. 9, l. 20, should read "(401)]"

Col. 9, l. 68, after "300°" delete the "+" symbol

Col. 10, l. 43, after "Table" change "1" to --3--

Signed and Sealed this

Tenth Day of August, 1993

Attest:

MICHAEL K. KIRK

Attesting Officer      Acting Commissioner of Patents and Trademarks